United States Patent [19]

Gross

[11] 4,124,022
[45] Nov. 7, 1978

[54] HEART NOVELTY AND RELAXATION DEVICE

[76] Inventor: Sam Gross, P.O. Box 1323, Hollywood, Calif. 91604

[21] Appl. No.: 759,335

[22] Filed: Jan. 14, 1977

[51] Int. Cl.² ...................... A61M 21/00; A61B 19/00
[52] U.S. Cl. ................................... 128/1 C; 128/422; 46/117; 46/232
[58] Field of Search ................. 128/1 C, 422; 46/117, 46/232, 226–229; 35/17; 200/11 DA, 164 A; D11/56, 83, 103; D10/6, 8; D14/31, 73

[56] References Cited

U.S. PATENT DOCUMENTS

| D. 67,506 | 3/1925 | Dietrich | D14/31 |
|---|---|---|---|
| D. 91,101 | 11/1933 | Covone | D10/6 |
| D. 211,894 | 8/1968 | Tokar | D10/6 |
| D. 243,470 | 2/1977 | Kleiner | D11/6 |
| 3,292,611 | 12/1966 | Belkin | 128/1 C |
| 3,563,229 | 10/1967 | Petrusson | 128/1 C |
| 3,570,473 | 3/1971 | Konvalin et al. | 128/422 |
| 3,629,525 | 12/1971 | Giese | 200/11 DA |
| 3,888,233 | 6/1975 | Ware | 46/232 |
| 3,994,282 | 11/1976 | Moulet | 46/232 |

FOREIGN PATENT DOCUMENTS 1,211,509  11/1970  United Kingdom ............... 200/11 DA

OTHER PUBLICATIONS

Lancaster; D., TTL Cookbook, Chapter 4, H. W. Sams Co., Indianapolis, 1976, pp. 171–175.
Neilson; G., Dupont Magazine, May–Jun. 1977, v. 71, No. 3, pp. 5–7.

*Primary Examiner*—Robert W. Michell
*Assistant Examiner*—Francis J. Jaworski
*Attorney, Agent, or Firm*—Spensley, Horn & Lubitz

[57] ABSTRACT

This heart novelty and relaxation device has a heart-shaped housing that contains a speaker and circuitry for producing a slow heartbeat sound which has a relaxing effect on a listener. The housing is assembled from two molded plastic conformal sides having integral complementary stanchions that mate to hold the sides together along a median plane. The circuitry is mounted on a board which also supports an on-off switch having a flat arm that pivots in the median plane. A portion of the switch arm projects unobtrusively from the housing through a slot at the interface between the sides to facilitate external control of the device.

3 Claims, 5 Drawing Figures

U.S. Patent    Nov. 7, 1978    4,124,022
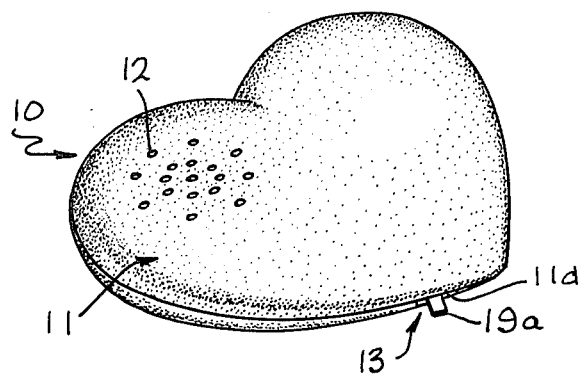
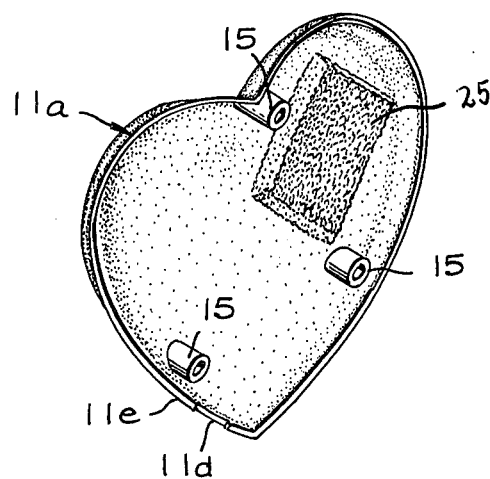
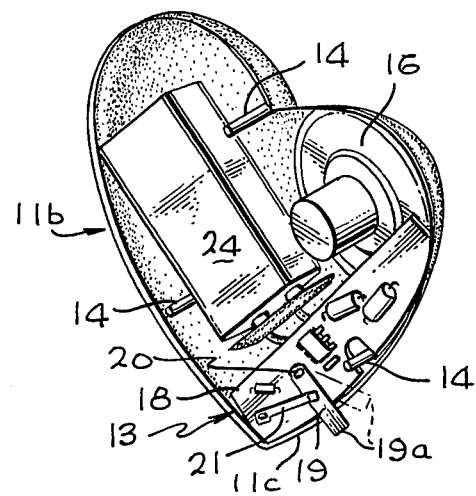
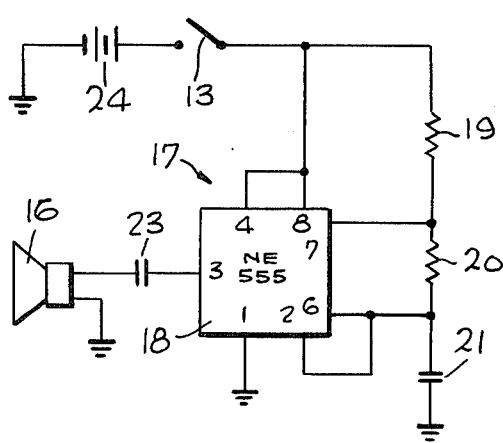
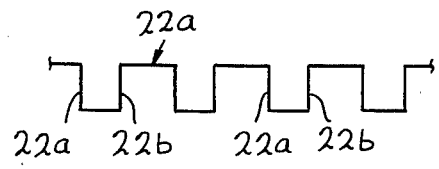

HEART NOVELTY AND RELAXATION DEVICE

BACKGROUND OF THE INVENTION

1. Field of the Invention

The present invention relates to a heart novelty and relaxation device including a heart-shaped housing containing circuitry for producing a sound simulating that of the human heartbeat at a slow rate.

2. Description of the Prior Art

The sound of a heart is recorded and played in many hospital nurseries. It recreates the sound of the mother's heart as heard by the child within the womb, and pacifies the infant. Adults, too, are calmed and relaxed by listening to a heartbeat sound, particularly at a slow rate. Such a slow heartbeat sound becomes a relaxant, a focus for meditation and an aid for insomniacs.

In the past, the use of a buzzer packaged in a casing has been used for soothing infants. Such an infant pacifying device is disclosed in the U.S. Pat. No. 2,932,821 to Horton. It employs a buzzer to produce an audible hum accompanied by mild vibration of the casing. The casing itself has a rounded dome-like shape that is free of protuberances.

An object of the present invention is to provide a relaxation device which produces a slow heartbeat sound. A further object is to provide such a device in a heart-shaped package in which the heart shape, the eternal symbol of love, complements the soothing heart sound.

SUMMARY OF THE INVENTION

These and other objectives are achieved by providing a heart novelty and relaxation device having a heart shaped molded plastic case containing a speaker and circuitry for producing a slow heartbeat sound. An on-off switch has a flat control arm that extends unobtrusively from the housing through a thin slot formed along the median plane thereof.

The circuitry advantageously comprises a free running multivibrator that provides a rectangular wave signal to the speaker. The repetition rate and duty cycle of this signal are selected so that the produced sound resembles the systolic and diastolic components of a human heartbeat at a pulse rate lower than the "normal" 72 beats per minute.

The housing advantageously is molded in two pieces. These form two conformal sides of the heart, separated along the median plane. The two sides include complementary mating stanchions that hold the sides together. The on-off switch is mounted on a circuit board within the housing, and includes a flat metal arm which is pivotally mounted to the board along the median plane. The arm serves both as an electrical member of the switch, and as the externally projecting control.

BRIEF DESCRIPTION OF THE DRAWINGS

A detailed description of the invention will be made with reference to the accompanying drawings wherein like numerals designate corresponding parts in the several figures.

FIG. 1 is a pictorial view of a heart novelty and relaxation device in accordance with the present invention.

FIG. 2 is a plan view of the interior of one of the two conformal sides of the housing for the device of FIG. 1.

FIG. 3 is a plan view of the interior of the other housing side, showing the speaker, circuit board and battery components.

FIG. 4 is an electrical schematic diagram of the circuitry for producing a slow heartbeat sound.

FIG. 5 is a waveshape of the signal supplied to the speaker by the circuitry of FIG. 4.

DESCRIPTION OF THE PREFERRED EMBODIMENT

The following detailed description is of the best presently contemplated mode of carrying out the invention. This description if not to be taken in a limiting sense, but is made merely for the purpose of illustrating the general principles of the invention since the scope of the invention is best defined by the appended claims.

The inventive heart novelty and relaxation device 10 is shown in FIG. 1. The device comprises a three dimensional heart-shaped housing 11 having a set of holes 12 through which a slow heartbeat sound emerges when a switch 13 is turned on.

The housing 11 advantageously is molded in two pieces 11a, 11b (FIGS. 2 and 3 respectively) which comprise two conformal sides of the heart-shaped housing 11, separated along the median plane. The side 11b includes a set of integrally molded stanchions 14 that mate within a complementary set of cylindrical stanchions 15 integrally formed in the side 11a. Press-fit or snap-together assembly of the two sides 11a, 11b is facilitated by the mating stanchions 14, 15.

Housed within the device 10, behind the openings 12, is a speaker 16 (FIG. 3). The speaker 16 is driven by an electrical circuit 17 (FIG. 4) the components of which are mounted on a circuit board 18. Advantageously, the upper surface of the circuit board 18 is situated in the median plane that separates the two sides 11a, 11b. This permits a very simplified construction for the switch 13.

As seen in FIG. 3, the switch 13 includes a flat metal arm 19 which is pivotally attached to the circuit board 18 as by means of a grommet 20. The arm 19 lies in the median plane, and is free to pivot just above the edge 11c of the housing side 11b. When the housing 11 is assembled, the end 19a of the arm 19 projects unobtrusively from the device 10 through a slot 11d formed at the edge 11e of the other housing side 11a. The other component of the switch 13 is a spring metal contact 21. To turn the device 10 on, the arm 19 is pivoted under the contact 21, as shown in solid in FIG. 3. To turn the device off, the arm 19 is swung away from the contact 21, as shown in phantom in FIG. 3.

Referring to FIG. 4, the circuit 17 utilizes an integrated circuit timer 18 such as that sold commercially by Signetics and others as type NE 555. When connected as shown in FIG. 4, the timer 18 operates as a free running multivibrator having a duty cycle and repetition rate established by the values of a pair of resistors 19, 20 and a capacitor 21. The output rectangular wave signal 22 (FIG. 5) is supplied to the speaker 16 via a capacitor 23. A battery 24, (FIG. 3) powers the circuit 17 and is held in place by a resilient pad 25.

In accordance with the present invention, the values of the resistors 19, 20 and the capacitor 21 are selected so that the rectangular wave signal 22 has a repetition rate that is less than the "normal" human heart rate of about 72 beats per minute. A particularly relaxing sound is obtained with a pulse rate on the order of from about 60 to 65 beats per minute.

The speaker 16 produces a pulse sound at each transition 22a, 22b of the rectangular wave signal 22. Preferably, the duty cycle of this rectangular wave 22 is selected so that the two sound pulses produced at each cycle simulate the systolic and diastolic components of a human heartbeat. In this manner, the sound produced by the device 10 is relaxing and has a calming effect to the listener. Thus, the device 10 can be used as a "drugless tranquilizer", as a focus for meditation, to sooth a baby, or as an aid to an insomniac.

Intending to claim all novel, useful and unobvious features, shown or described, the inventor claims:

1. A heart novelty and relaxation device comprising:
   a molded plastic housing of heart shape, said housing having two conformal sides separated along a median plane and adapted for press-together assembly,
   a speaker within said housing,
   an electrical circuit within said housing for providing to said speaker a signal to simulate the sound of the human heartbeat at a slow pulse rate,
   an on-off switch for said circuit, said switch being mounted within said housing and having a flat control arm extending unobtrusively from said housing through a thin longitudinal slot formed along said median plane, and wherein
   said electrical circuit is mounted on a circuit board situated adjacent said median plane, said switch arm consisting of a flat strip of metal lying in said median plane and pivotally mounted to said circuit board by a conductive pivot member extending through said metal strip and said circuit board, said switch also having a spring metal contact fixedly mounted to said circuit board, said switch arm pivoting about said pivot member in said median plane into engagement with said spring metal contact to close said switch via an electrical path including said pivot member, said switch arm and contact.

2. A heart novelty and relaxation device according to claim 1 wherein said two housing sides include integrally molded, complementary mating stanchions, the stanchions of one housing side being matingly received by the complementary stanchions of the other housing side to accomplish said snap-together assembly.

3. A heart novelty and relaxation device according to claim 2 wherein said electrical circuit comprises a free running multivibrator that produces a single rectangular wave signal causing said speaker to produce two sound beats per cycle, one at each transition of said rectangular wave signal, the duty cycle of said rectangular wave signal being selected so that the sound beats resemble both the systolic and diastolic components of a human heartbeat, at a pulse rate lower than about 72 beats per minute.

* * * * *